United States Patent [19]

Schmidt et al.

[11] Patent Number: 4,625,024

[45] Date of Patent: Nov. 25, 1986

[54] PROCESS FOR THE PREPARATION OF 6-METHYL-3,4-DIHYDRO-1,2,3-OXATHIA-ZIN-4-ONE 2,2-DIOXIDE AND ITS NON-TOXIC SALTS

[75] Inventors: Erwin Schmidt; Karl Clauss, both of Kelkheim, Fed. Rep. of Germany

[73] Assignee: Hoechst Aktiengesellschaft, Frankfurt am Main, Fed. Rep. of Germany

[21] Appl. No.: 762,563

[22] Filed: Aug. 5, 1985

[30] Foreign Application Priority Data

Aug. 7, 1984 [DE] Fed. Rep. of Germany ....... 3429039

[51] Int. Cl.$^4$ ........................................... C07D 291/06
[52] U.S. Cl. ........................................................ 544/2
[58] Field of Search ............................................ 544/2

[56] References Cited

U.S. PATENT DOCUMENTS

| | | | |
|---|---|---|---|
| 3,689,486 | 9/1972 | Clauss et al. | 544/2 |
| 3,917,589 | 11/1975 | Clauss et al. | 544/2 |
| 3,968,107 | 7/1976 | Clauss et al. | 544/2 |
| 3,969,347 | 7/1976 | Schmidt et al. | 544/2 |
| 4,052,453 | 10/1977 | Pietsch et al. | 260/543 F |
| 4,563,521 | 1/1986 | Clauss et al. | 544/2 |

OTHER PUBLICATIONS

Clauss et al., "Oxathiazinone Dioxides—A New Group of Sweetening Agents", Angew. Chem. International Edition, vol. 12 (11), pp. 869–876 (1973).

Tullock et al., "Synthesis of Fluorides by Metathesis with Sodium Fluoride", Chem. Abstracts, vol. 55 (11), 18551g–18552e (Sep. 1961).

*Primary Examiner*—John M. Ford
*Attorney, Agent, or Firm*—Curtis, Morris & Safford

[57] ABSTRACT

6-Methyl-3,4-dihydro-1,2,3-oxathiazin-4-one 2,2-dioxide and its non-toxic salts are prepared by reacting acetoacetamide with an S–O compound of the formula I $$FSO_2Y \qquad (I)$$

wherein Y=F, Cl, —OSO$_2$F or —OSO$_2$Cl, preferably only F, in the presence of bases.

The non-toxic salts—especially the potassium salt—are valuable synthetic sweeteners.

15 Claims, No Drawings

PROCESS FOR THE PREPARATION OF 6-METHYL-3,4-DIHYDRO-1,2,3-OXATHIAZIN-4-ONE 2,2-DIOXIDE AND ITS NON-TOXIC SALTS

6-Methyl-3,4-dihydro-1,2,3-oxathiazin-4-one 2,2-dioxide is the compound of the formula

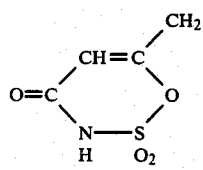

As a result of the acid hydrogen on the nitrogen atom, the compound is capable of forming salts (with bases). Because of their sweet taste, which is intense in some cases, the non-toxic salts—for example the Na, K and Ca salts, can be used as sweeteners in the food industry, the K salt ("Acesulfam K" or simply "Acesulfam") being of particular importance.

A number of different processes are known for the preparation of 6-methyl-3,4-dihydro-1,2,3-oxathiazin-4-one 2,2-dioxide and its non-toxic salts; cf. Angewandte Chemie 85, volume 22 (1973), pages 965 to 73, corresponding to International Edition volume 12, no. 11 (1973), pages 869–76. Virtually all processes use chlorosulfonyl or fluorosulfonyl isocyanate ($XSO_2NCO$ with $X=Cl$ or F) as the starting material. The chlorosulfonyl or fluorosulfonyl isocyanate is then reacted with monomethylacetylene, acetone, acetoacetic acid, tert.-butyl acetoacetate or benzyl propenyl ether (generally in a multistep reaction) to give N-chlorosulfonylacetoacetamide or N-fluorosulfonylacetoacetamide, which cyclizes under the action of bases (for example methanolic KOH) and gives the corresponding salts of 6-methyl-3,4-dihydro-1,2,3-oxathiazin-4-one 2,2-dioxide. If desired, the free oxathiazinone can be obtained from the salts in the usual manner (with acids).

Another process for the preparation of the oxathiazinone intermediate N-fluorosulfonylacetoacetamide starts from amidosulfonyl fluoride, $H_2NSO_2F$, the product of partial hydrolysis of fluorosulfonyl isocyanate (DE-OS No. 2 453 063). In this process, the fluoride of amidosulfonic acid, $H_2NSO_2F$, is reacted with an approximately equimolar quantity of the acetoacetylating agent diketen, in an inert organic solvent, in the presence of an amine, at temperatures of between about $-30°$ and $100°$ C.; the reaction proceeds according to the following equation (with triethylamine as the amine):

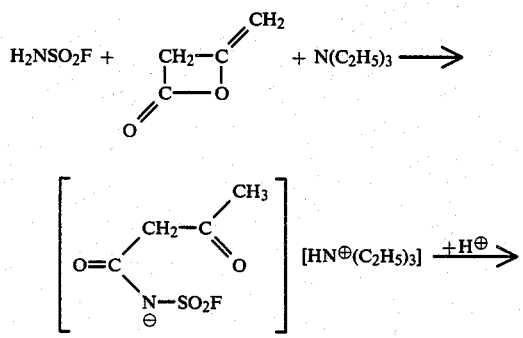

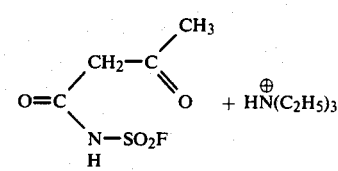

N—fluorosulfonylacetoacetamide

The N-fluorosulfonylacetoacetamide is then cyclized in the usual manner by means of a base, for example with methanolic KOH, to give the sweetener:

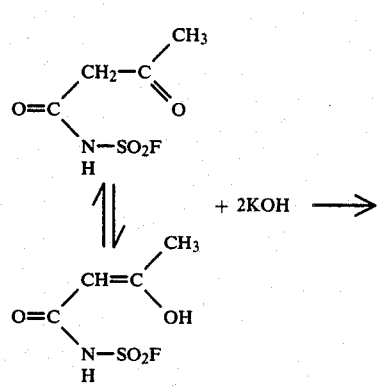

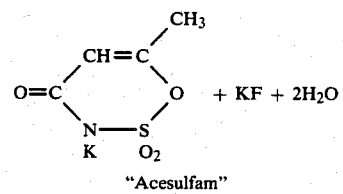

"Acesulfam"

Although the known processes in some cases give very satisfactory yields of 6-methyl-3,4-dihydro-1,2,3-oxathiazin-4-one 2,2-dioxide and its non-toxic salts (up to approx. 85% of theory, based on the starting amidosulfonic acid halide), they are still in need of improvement, especially for industrial purposes, because of the necessity of using chlorosulfonyl or fluorosulfonyl isocyanate as starting materials, which are not altogether easy to obtain; in fact, the preparation of chlorosulfonyl and fluorosulfonyl isocyanates requires considerable precautionary measures and safety precautions because of the fact that the starting materials are in some cases rather unpleasant to handle—in particular HCN and HF. The preparation of chlorosulfonyl and fluorosulfonyl isocyanates is based on the following equations.

$HCN + Cl_2 \rightarrow ClCN + HCl$ $ClCN + SO_3 \rightarrow ClSO_2NCO$ $ClSO_2NCO + HF \rightarrow FSO_2NCO + HCl$ It has therefore already been suggested, inter alia, to prepare 6-methyl-3,4-dihydro-1,2,3-oxathiazin-4-one 2,2-dioxide and its non-toxic salts by reacting acetoacetamide with at least about twice the molar quantity of $SO_3$, if appropriate in an inert inorganic or organic solvent and if appropriate with subsequent neutralization, with a base, of the 6-methyl-3,4-dihydro-1,2,3-oxathiazin-4-one 2,2-dioxide thereby produced in the acid form (Patent Application U.S.-Ser. No. 714,175).

In the reaction, N-sulfoacetoacetamide is probably formed first from one mol of acetoacetamide and one mol of SO₃, and this is then cyclized with a further mol of SO₃ to give 6-methyl-3,4-dihydro-1,2,3-oxathiazin-4-one 2,2-dioxide:

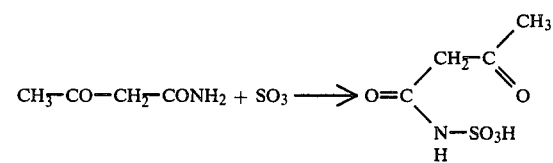

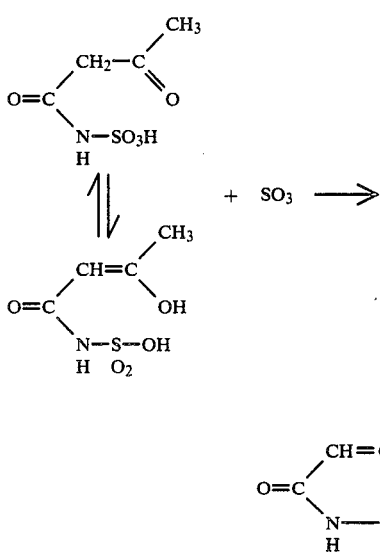

If it is intended to obtain salts, the 6-methyl-3,4-dihydro-1,2,3-oxathiazin-4-one 2,2-dioxide can then be neutralized—for example with KOH:

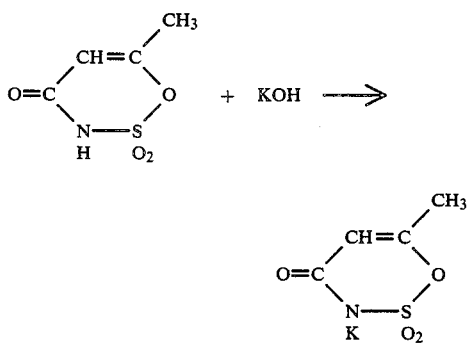

Yields of about 30 to about 90% of theory, based on the acetoacetamide, are obtained here.

If acetoacetamide is reacted with sulfuryl chloride, $SO_2Cl_2$, instead of $SO_3$, α-chlorination of the acetoacetamide takes place to give the α,α-dichlorinated product $CH_3$—CO—$CCl_2$—$CONH_2$, which is cleaved with bases according to the following equation: $CH_3$—CO—$CCl_2$—$CONH_2$+NaOH→$CH_3COONa$+$HCCl_2$-$CONH_2$; cf. JP-OS 73-39431, ref. in C.A. volume 79 (1973), 65827a.

Surprisingly, it has now been found that sulfuryl fluoride, as well as some other special fluorosulfonyl compounds, react with acetoacetamide and bases in a completely different way, i.e. to form 6-methyl-3,4-dihydro-1,2,3-oxathiazin-4-one 2,2-dioxide or its corresponding salts.

The invention therefore relates to a process for the preparation of 6-methyl-3,4-dihydro-1,2,3-oxathiazin-4-one 2,2-dioxide and its non-toxic salts starting from acetoacetamide and an S-O compound, which comprises reacting acetoacetamide with an S-O compound of the formula I $$FSO_2Y \qquad (I)$$

wherein Y=F, Cl, —$OSO_2F$ or —$OSO_2Cl$, preferably only F, in the presence of bases. The reaction is based on the following equation (with $K_2CO_3$ as the base):

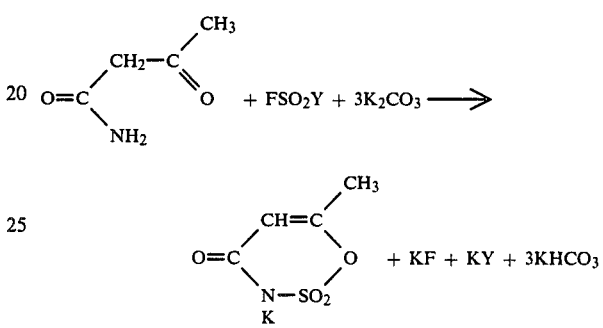

The yields obtainable by the process are of the same order of magnitude as the yield of the process of the abovementioned patent application and are between about 20 and 90% of theory, based on the starting acetoacetamide.

Acetoacetamide is obtainable for example from acetoacetyl chloride or diketen and $NH_3$ and is furthermore a common commercial product.

The compounds covered by the formula I are sulfuryl fluoride, $SO_2F_2$, chlorosulfonyl fluoride, $SO_2ClF$, pyrosulfuryl fluoride, $FSO_2$—O—$SO_2F$, and chloropyrosulfuryl fluoride, $ClSO_2$—O—$SO_2F$; the preferred compound of the formula I is sulfuryl fluoride, $SO_2F_2$.

These sulfuryl halides are prepared by known processes. For example, $SO_2F_2$ and $SO_2ClF$ can be obtained by heating $SO_2Cl_2$ with NaF to temperatures of about 60° to 80° C. (C. W. Tullock and D. D. Coffman, J. Org. Chem. 25, page 2016 (1960)).

In principle, all possible substances giving a basic reaction can be used as bases for the process according to the invention; however, it is preferred to use tertiary amines having a total of up to 15 C atoms, as well as basic ion exchangers and the oxides, hydroxides, carbonates and hydrogencarbonates of alkali and alkaline earth metals.

Examples of tertiary amines are: trimethylamine, triethylamine, N-ethyldiisopropylamine, benzyldimethylamine, dimethylaniline, N,N-dimethylpiperazine, N-ethylpiperidine, pyridine, α-, β- and γ-picoline, diazabicyclooctane, diazabicycloundecene, etc.

Basic ion exchangers which can be used are the commercially available products.

The following may be mentioned as examples of oxides, hydroxides, carbonates and hydrogencarbonates of alkali and alkaline earth metals:
LiOH, $Li_2CO_3$, $LiHCO_3$,
NaOH, $Na_2CO_3$, $NaHCO_3$,
KOH, $K_2CO_3$, $KHCO_3$, CaO, Ca(OH$_2$), CaCO$_3$, Ca(HCO$_3$)$_2$, etc.

Particularly preferred bases are tertiary amines having a total of up to only 10 C atoms and the hydroxides and carbonates of Na and K. K$_2$CO$_3$ is very particularly preferred because it enables Acesulfam K to be obtained in a particularly easy manner.

Combinations of several bases are also possible, for example a tertiary amine is used first, this being followed by the action of an alkali metal hydroxide.

The acetoacetamide and the S-O compounds of the formula I are preferably used in a molar ratio of about 1:(1-1.5) for the process according to the invention; for complete cyclization, at least about 3 and preferably about 3-5 equivalents of base are used per mol of acetoacetamide. This gives the 6-methyl-3,4-dihydro-1,2,3-oxathiazin-4-one 2,2-dioxide in the form of a salt from which, if desired, the acid form can be obtained in the usual manner, for example by means of mineral acids (hydrochloric acid, sulfuric acid, etc.), acid salts (KHSO$_4$ etc.) or acid ion exchangers.

The reaction according to the invention can be carried out either in the absence or in the presence of inert solvents and diluents, i.e. solvents and diluents which do not react in an undesirable way with the starting materials and end products under the reaction conditions.

Both protic and aprotic organic solvents are suitable, such as lower alcohols (methanol, ethanol, i-propanol, tert.-butanol, etc.), lower aliphatic halogenohydrocarbons (ethylene chloride, 1,2-dichloroethane, chloroform, carbon tetrachloride, tetrachloroethylene, etc.), aromatic chlorohydrocarbons (chlorobenzene, chlorotoluene, etc.), ketones (acetone, ethyl methyl ketone, cyclohexanone, acetophenone, etc.), aliphatic carboxylic acid esters (ethyl acetate, butyl acetate, methyl propionate, diethyl malonate, dimethyl succinate, methoxyethyl acetate, glycol monoacetate, glycol diacetate, ethyl cyanoacetate, etc.), aromatic carboxylic acid esters (methyl benzoate, ethyl benzoate, etc.), aliphatic carboxamides (dimethylformamide, dimethylacetamide, etc.), urea derivatives (tetramethylurea, tetrabutylurea, etc.) and aliphatic and aromatic nitriles (acetonitrile, benzonitrile, etc.).

The solvents and diluents can be used either individually or in mixtures with one another (even in the region of miscibility gaps).

It is also possible to use inorganic solvents, for example liquid SO$_2$, and, if appropriate, water. However, it is not possible to use water if Cl-containing products and pyrosulfuryl fluoride are used as compounds of the formula I, because they hydrolyze rapidly and easily with water. Sulfuryl fluoride is relatively stable to water—at least if the temperatures are not too high.

Preferred solvents are acetonitrile and aqueous acetone, especially aqueous acetone with a water content of about 1 to 12% by weight.

In principle, the quantity of solvent or diluent is not critical and it should be determined so that the reaction mixture is easy to stir. The upper limit to the quantity of solvent or diluent is determined mainly by economic considerations; solutions which are too dilute are no longer advantageous.

The reaction temperature can also be varied within a fairly wide range. Depending on the choice of bases and solvents or diluents, the reaction can be carried out from about $-70°$ C. to about the boiling point of the solvent or diluent. The reaction rate decreases at lower temperatures and the yield decreases at excessively high temperatures. In general, the common temperature range is between about $-70°$ and $+100°$ C., preferably between about $-10°$ and $+60°$ C.

The most advantageous reaction pressure is generally atmospheric pressure, although it is also possible to carry out the reaction under excess pressure; a reduced pressure is less suitable.

To carry out the reaction according to the invention, it is possible in principle to meter the reaction components into the reaction vessel successively, in any order, or simultaneously. An advantageous embodiment consists in introducing the acetoacetamide and the base(s), if appropriate dissolved in an inert solvent or diluent, and metering in the S-O compound of the formula I.

The reaction mixture is worked up in the usual manner.

The invention is of considerable economic value because of the simple starting materials and the ease with which the reaction can be carried out, and also because of the very high yields in some cases.

The invention will now be illustrated in greater detail by means of the examples which follow.

EXAMPLE 1

A solution of 10.1 g (0.1 mol) of acetoacetamide and 33.0 g (0.33 mol) of triethylamine in 100 ml of acetonitrile was introduced into a round-bottomed flask fitted with a stirrer and a solid carbon dioxide condenser. 10.2 g (0.1 mol) of sulfuryl fluoride gas were then passed in at $-70°$ C. over a period of 30 minutes.

The reaction mixture was subsequently stirred for 3 hours, during which time it was allowed to warm up to room temperature. The reaction mixture was then added dropwise to 90 ml of 4N methanolic KOH and the product was filtered off with suction. 7.2 g (36% of theory) of Acesulfam K were obtained, the IR spectrum of which was identical to that of a reference material.

EXAMPLE 2

10.1 g (0.1 mol) of acetoacetamide, 50.5 g (0.5 mol) of triethylamine and 100 ml of acetonitrile were introduced into a round-bottomed flask fitted with a stirrer and a solid carbon dioxide condenser, as in Example 1. 15.3 g (0.15 mol) of sulfuryl fluoride gas were passed in over a period of 20 minutes. The reaction mixture was then allowed to warm up to room temperature, with stirring. After stirring for 2 hours, 230 ml (0.46 mol) of 2N methanolic KOH were added dropwise and the product was filtered off with suction. 9.7 g (48% of theory) of Acesulfam K were obtained.

EXAMPLE 3

A mixture, with a total volume of 50 ml, of 40.4 g (0.4 mol) of triethylamine and liquid SO$_2$ was added dropwise, at $-10°$ C., to a solution of 20.2 g (0.2 mol) of acetoacetamide and 23.7 g (0.2 mol) of chlorosulfonyl fluoride in 70 ml of liquid SO$_2$. The mixture was stirred for 2 hours and the liquid SO$_2$ was then distilled off, a vacuum being applied at the end. The residue was added dropwise to 400 ml of aqueous NaOH, acidified with concentrated hydrochloric acid, with ice-cooling, and extracted with ethyl acetate. After treatment of the ethyl acetate phase with animal charcoal and Na$_2$SO$_4$, the extract was evaporated in vacuo. 15 g (approx. 20% of theory) of 6-methyl-3,4-dihydro-1,2,3-oxathiazin-4-one 2,2-dioxide were obtained.

EXAMPLE 4

Different quantities of water were added to 150 ml of acetone. 10.1 g (0.1 mol) of acetoacetamide and 69 g (0.5 mol) of finely powdered, dry $K_2CO_3$ were added to each of these mixtures. 15.3 g (0.15 mol) of sulfuryl fluoride gas were then passed in—initially at room temperature. The temperature of the reaction mixture increased to about 40° C. during this process. The mixture was stirred for a further 2 hours and the product was filtered off with suction. The filter residue contained Acesulfam K, which was found to be identical to a reference sample by thin layer chromatography (silica gel, solvent system: ethyl acetate/glacial acetic acid 5:1). The filter residue was introduced into a mixture of excess hydrochloric acid with ice and extracted with ethyl acetate. The ethyl acetate extract was dried over $Na_2SO_4$ and evaporated in vacuo. Crystalline 6-methyl-3,4-dihydro-1,2,3-oxathiazin-4-one 2,2-dioxide was obtained and this was converted to Acesulfam K with methanolic KOH. The results are collated in the table which follows. In the last experiment listed in the table, the $K_2CO_3$ was used as a 50% aqueous solution.

TABLE

| Quantity of water added | | Yield of Acesulfam K | |
|---|---|---|---|
| (ml) | % by weight, based on acetone | g | % of theory |
| 0 | — | 3.75 | 23 |
| 2 | 1.7 | 10.86 | 67 |
| 6 | 5.1 | 12.15 | 75 |
| 8 | 6.7 | 14.10 | 86.5 |
| 10 | 8.4 | 12.20 | 75 |
| 12 | 10.1 | 11.54 | 71 |
| 14 | 11.8 | 8.3 | 51 |
| 69 | 58 | 6.4 | 39 |

What is claimed is:

1. A process for the preparation of 6-methyl-3,4-dihydro-1,2,3,-oxathiazin-4-one 2,2-dioxide and its non-toxic salts, which comprises reacting acetoacetamide with an S-O compound of the formula I $$FSO_2Y \quad (I)$$

wherein Y=F, Cl, —$OSO_2F$ or —$OSO_2Cl$, in the presence of a base.

2. The process as claimed in claim 1, wherein the S-O compound of the formula I is $SO_2F_2$.

3. The process as claimed in claim 1, wherein the base is selected from the group consisting of tertiary amines having a total of up to 15 C atoms, basic ion exchangers and the oxides, hydroxides, carbonates and hydrogencarbonates of alkali and alkaline earth metals.

4. The process as claimed in claim 1, wherein the base is selected from the group consisting of tertiary amines having a total of up to 10 C atoms and the hydroxides and carbonates of Na and K.

5. The process as claimed in claim 1, wherein the base is $K_2CO_3$.

6. The process as claimed in claim 1, wherein about 1 to 1.5 mol of the S-O compound of the formula I and at least about 3 equivalents of base are used per mol of acetoacetamide.

7. The process as claimed in claim 1, wherein about 1 to 1.5 mol of the S-O compound of the formula I and about 3 to 5 equivalents of base are used per mol of acetoacetamide.

8. The process as claimed in claim 1, wherein the reactions is carried out in the presence of inert solvents or diluents.

9. The process as claimed in claim 1, wherein the reaction is carried out in the presence of $CH_3CN$.

10. The process as claimed in claim 1, wherein the reaction is carried out in the presence of aqueous acetone.

11. The process as claimed in claim 1, wherein the reaction is carried out in the presence of aqueous acetone with a water content of about 1 to 12% by weight.

12. The process as claimed in claim 1, wherein the reaction is carried out at a temperature of between about −70° and +100° C.

13. The process as claimed in claim 1, wherein the reaction is carried out at a temperature of between about −10° and +60° C.

14. The process as claimed in claim 1, wherein the S-O compound of the formula I is metered in to the acetoacetamide and the base.

15. The process as claimed in claim 14, wherein the acetoacetamide and the base are dissolved in an inert solvent or diluent.

* * * * *